(12) United States Patent
Takino

(10) Patent No.: US 8,945,078 B2
(45) Date of Patent: Feb. 3, 2015

(54) WEARING ARTICLE

(75) Inventor: Shunsuke Takino, Kagawa (JP)

(73) Assignee: Unicharm Corporation, Ehime (JP)

( * ) Notice: Subject to any disclaimer, the term of this patent is extended or adjusted under 35 U.S.C. 154(b) by 114 days.

(21) Appl. No.: 13/518,969

(22) PCT Filed: Dec. 16, 2010

(86) PCT No.: PCT/JP2010/072642
§ 371 (c)(1),
(2), (4) Date: Jun. 25, 2012

(87) PCT Pub. No.: WO2011/078051
PCT Pub. Date: Jun. 30, 2011

(65) Prior Publication Data
US 2012/0271269 A1    Oct. 25, 2012

(30) Foreign Application Priority Data

Dec. 25, 2009 (JP) ................................. 2009-296186

(51) Int. Cl.
*A61F 13/493* (2006.01)
(Continued)

(52) U.S. Cl.
CPC .......... *A61F 13/551* (2013.01); *A61F 13/15747* (2013.01); *A61F 13/49466* (2013.01); *A61F 13/496* (2013.01)
USPC ........... 604/385.201; 604/385.25; 604/385.01

(58) Field of Classification Search
CPC ................ A61K 6/00; A61F 13/49009; A61F 13/49011; A61F 13/49012; A61F 13/49014; A61F 13/49015; A61F 13/49017; A61F 2013/49038; A61F 2013/49039; A61F 2013/49041; A61F 13/494; A61F 13/49406; A61F 13/49413; A61F 13/49446; A61F 13/49453; A61F 2013/4948

See application file for complete search history.

(56) References Cited

U.S. PATENT DOCUMENTS

2008/0004586 A1 * 1/2008 Lodge et al. ............. 604/385.03

FOREIGN PATENT DOCUMENTS

| JP | 2006-043325 | 2/2006 |
| JP | 2006-055462 | 3/2006 |

(Continued)

OTHER PUBLICATIONS

Prada, E., et al. "Zero Laundau Level in Folded Graphene Nanoribbons", Physical Review Letters: Sep. 3, 2010.*
International Search Report from corresponding PCT application No. PCT/JP2010/072642 dated Mar. 22, 2011 (2 pgs).

*Primary Examiner* — Tatyana Zalukaeva
*Assistant Examiner* — Sara Sass
(74) *Attorney, Agent, or Firm* — Brinks Gilson & Lione

(57) ABSTRACT

A wearing article having a chassis bent in a crotch region. A diaper is folded along an imaginary lateral center line so that front and rear waist regions are in contact with each other and so that front and rear upper end edges in the regions substantially have the same level with each other. In such a folded state, first folds extending in the longitudinal direction are defined in portions of gasket cuffs which are biased toward the front waist region relative to the imaginary lateral center line. The first folds are defined along lateral edges of core of a liquid absorbent structure, and the gasket cuffs being located outboard of the lateral edges are folded along the first folds onto a garment-facing side of an outer sheet. Second folds which extend in the longitudinal direction are formed in containment cuffs. The second folds are lying on a side closer to the front waist region in relation to the imaginary lateral center line, and folded distal ends are expanded and folded to the garment-facing side of the outer sheet.

12 Claims, 7 Drawing Sheets

(51) Int. Cl.
  *A41B 9/00* (2006.01)
  *A61F 13/551* (2006.01)
  *A61F 13/15* (2006.01)
  *A61F 13/494* (2006.01)
  *A61F 13/496* (2006.01)

(56) References Cited

FOREIGN PATENT DOCUMENTS

| | | |
|---|---|---|
| JP | 2009-528888 A | 8/2009 |
| JP | 2010-233797 | 10/2010 |

* cited by examiner

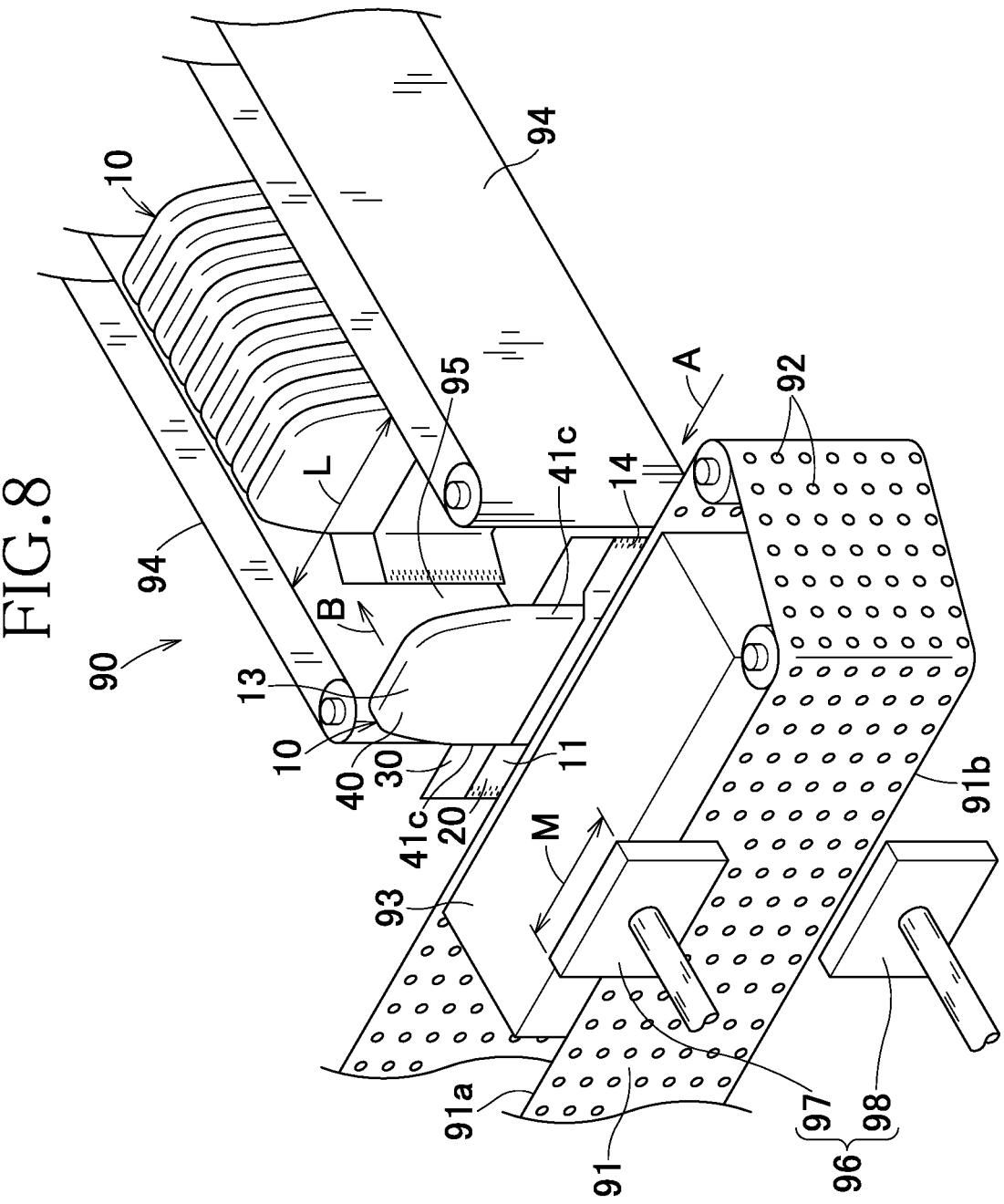

WEARING ARTICLE

RELATED APPLICATION

This application is a 35 U.S.C. §371 national phase filing of International Patent Application No. PCT/JP2010/072642, filed Dec. 16, 2010, through which and to which priority is claimed under 35 U.S.C. §119 to Japanese Patent Application No. 2009-296186, filed Dec. 25, 2009.

TECHNICAL FIELD

The present invention relates to wearing articles, and more specifically, relates to wearing articles such as disposable diapers, toilet training pants, incontinent briefs, or the like.

BACKGROUND

Conventionally, disposable diapers in which lateral edges thereof are folded to a longitudinal center line when a plurality of diapers is contained in a package are known. For example, according to PTL 1, both a front waist region and a rear waist region of a chassis are folded such that a dimension in a lateral direction of the diaper becomes small.

CITATION LIST

Patent Literature

{PTL 1} JP 2009-528888 A

SUMMARY OF INVENTION

Technical Problem

According to the above PTL 1, a constitution in which both the front and rear waist regions are folded is disclosed, but folding in a crotch region is not disclosed.

An object of the present invention is to provide a wearing article in which a chassis is folded in a crotch region.

Solution to Problem

The present invention relates to an improvement of a wearing article having a longitudinal direction and a lateral direction, which includes:

a chassis including a skin-facing side facing the wearer's skin, an opposite side thereof, a first waist region that is one of front and rear waist regions;

a second waist region that is a remainder of the front and rear waist regions; and a crotch region extending between the first and second waist regions, wherein the chassis further includes first and second end edges extending in the lateral direction in the first and second waist regions and lateral edges extending in the longitudinal direction; and the lateral edges of the first and second waist regions are joined to each other such that a waist opening is defined in the first and second end edges and such that a pair of leg openings is defined in the lateral edges of the crotch region.

In the wearing article, the features of the present invention reside in that: the lateral edges are folded to the opposite side of the chassis along first folds extending in the longitudinal direction; and the first folds are at least in the crotch region and at a side closer to the first waist region in relation to an imaginary lateral center line that bisects a dimension in the longitudinal direction from the first end edge to the second end edge. According to the embodiment of the present invention, it is to be noted that the first folds are not formed on a side closer to the second waist region in the crotch region.

According to one embodiment of the present invention, the wearing article further includes a liquid absorbent structure extending from the crotch region to the first and second waist regions on the skin-facing side of the chassis, wherein the liquid absorbent structure includes a liquid absorbent core and a coating sheet to cover the core, and the first folds are defined along the lateral edges of the core.

According to another embodiment of the present invention, waist elastic elements are contractibly attached to the first waist region in a stretched state in the lateral direction, and the waist elastic elements are overlapped with at least the lateral edges of the core.

According to still another embodiment of the present invention, a pair of gasket cuffs is formed outboard of the liquid absorbent structure in the lateral direction, and gasket elastic elements are contractibly attached to the gasket cuffs in the longitudinal direction.

According to yet another embodiment of the present invention, the waist elastic elements and the gasket elastic elements are intersected with each other in the first waist region.

According to further another embodiment of the present invention, the liquid absorbent structure includes an upper surface facing the wearer's body and a bottom surface opposite thereto. Elasticized containment cuffs are contractibly attached to the upper surface in a stretched state in the longitudinal direction. Each of the containment cuffs includes a proximal edge continuous to the upper surface and a distal edge which is capable of being spaced apart from the upper surface. The distal edge is folded onto the opposite side of the chassis along the second folds extending in the longitudinal direction.

Advantageous Effects of Invention

According to the present invention, in particular, one or more embodiments thereof, the lateral edges of the chassis are folded to the opposite side to the skin-facing side along each of the first folds that is located at least in the crotch region and also located at the side closer to the first waist region in relation to an imaginary lateral center line bisecting a dimension in the longitudinal direction. Accordingly, when putting on the wearing article, the lateral edges are not extended into leg openings so as to cause the opening area smaller, and legs may be easily passed through, hence it is easy to wear. Moreover, since the first folds are defined only on the side closer to the first waist region in the crotch region, it is easy to distinguish the side of the first waist region.

BRIEF DESCRIPTION OF DRAWINGS

FIG. 8 is a schematic diagram of a device.

DESCRIPTION OF THE EMBODIMENTS

FIGS. 1-8 illustrate one embodiment of the present invention, which is described by exemplifying a disposable diaper as a wearing article.

Figure 1:
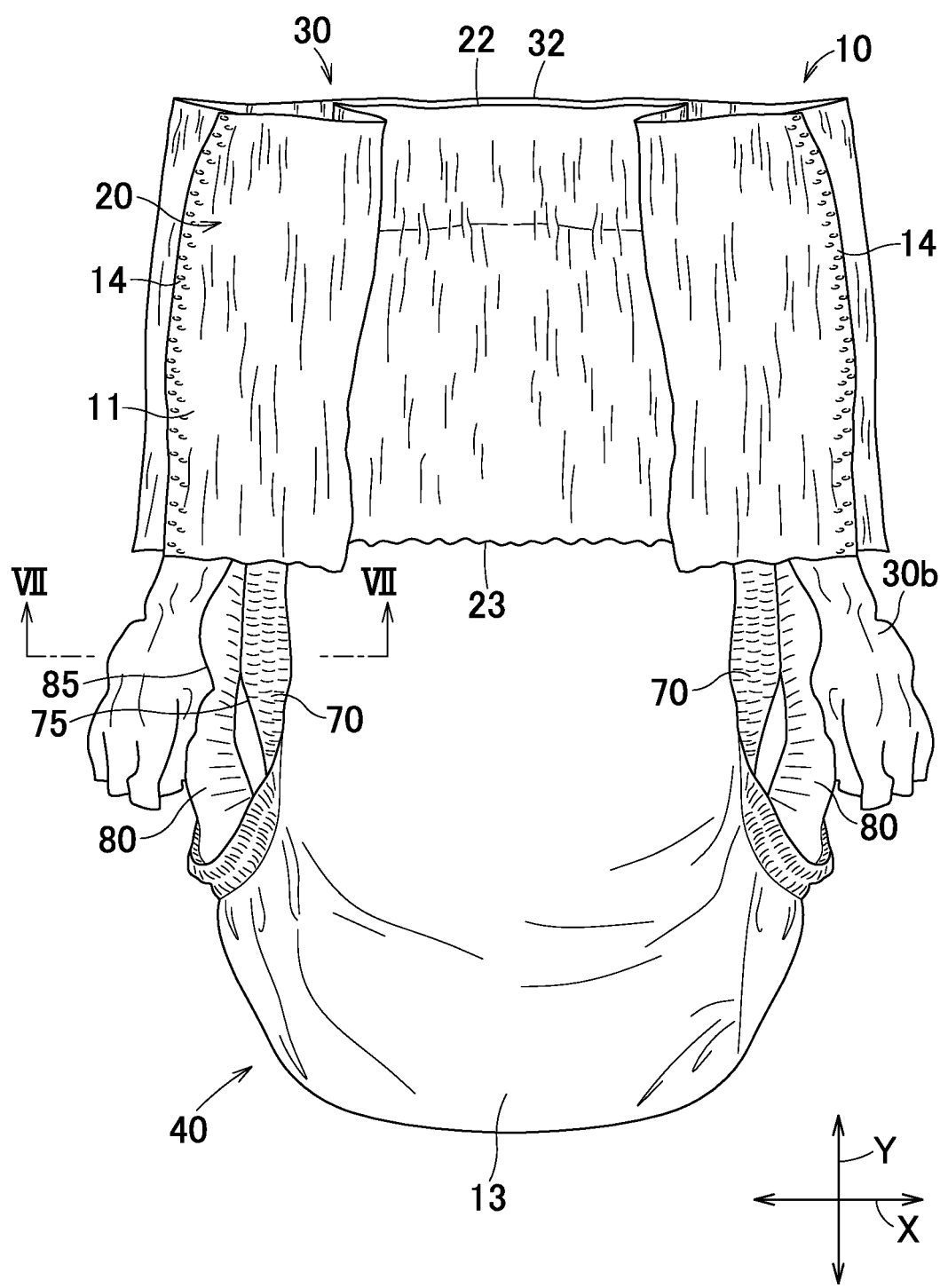
FIG. 1 is a planar view of a disposable diaper illustrated as one example of wearing articles.
Figure 2:
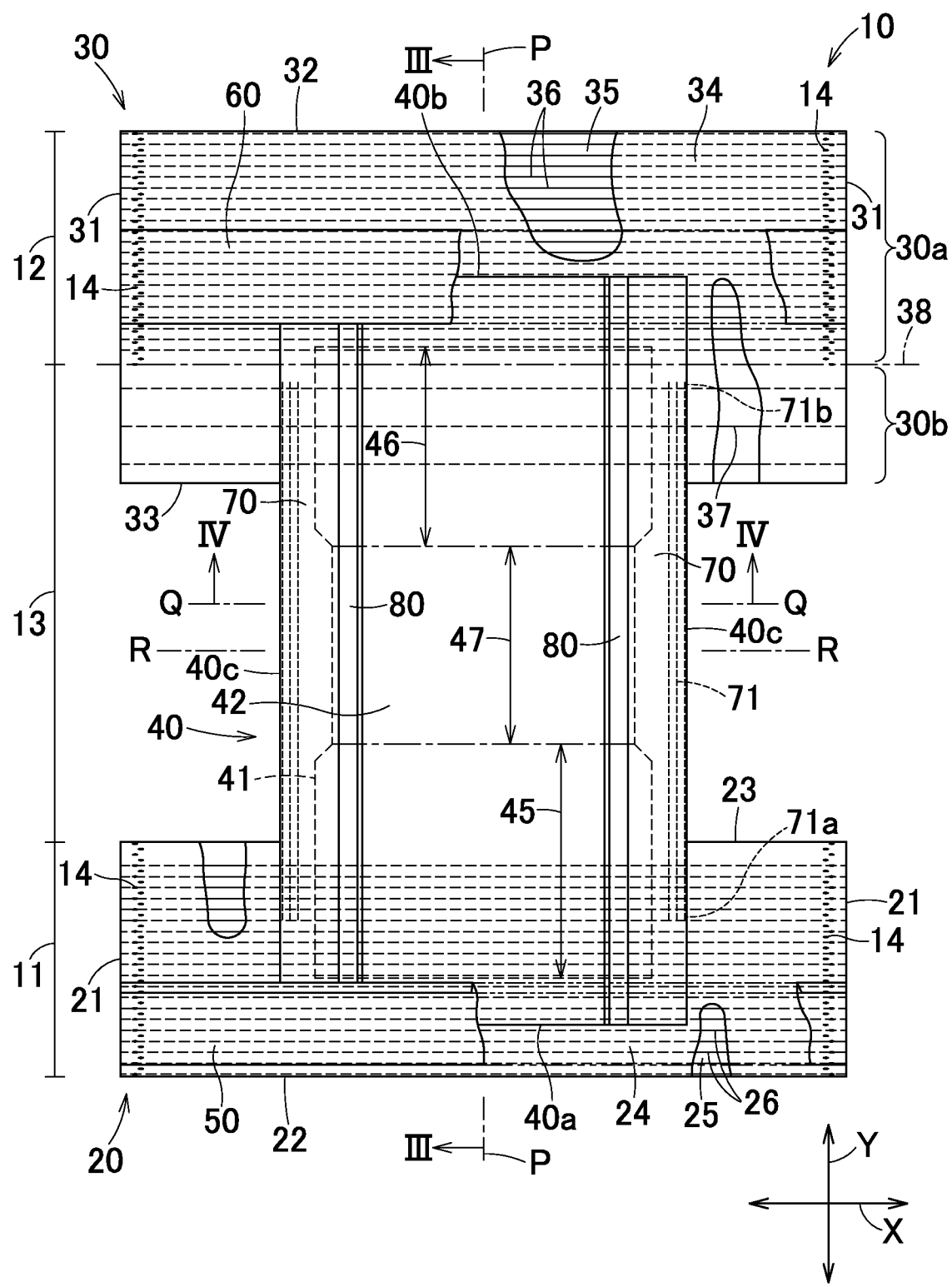
FIG. 2 is an extended planar view of the diaper.
Figure 3:
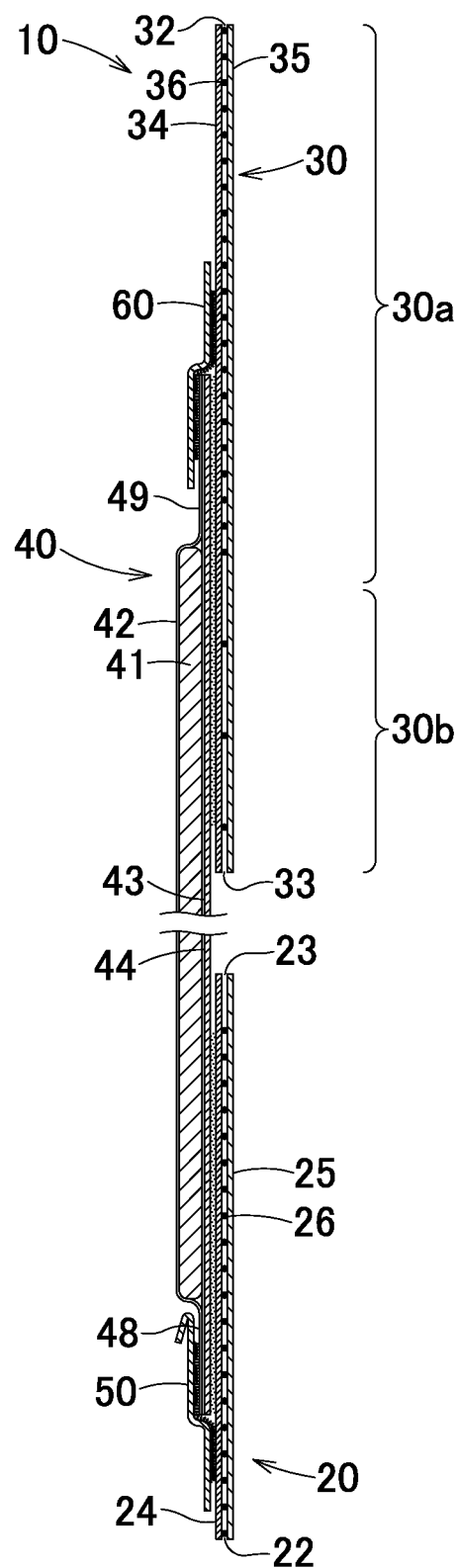
FIG. 3 is a cross section view along line of FIG. 2.
Figure 4:
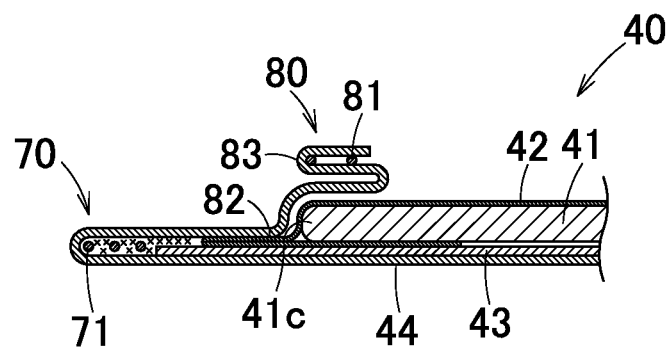
FIG. 4 is across section view along IV-IV line of FIG. 2.
Figure 5:
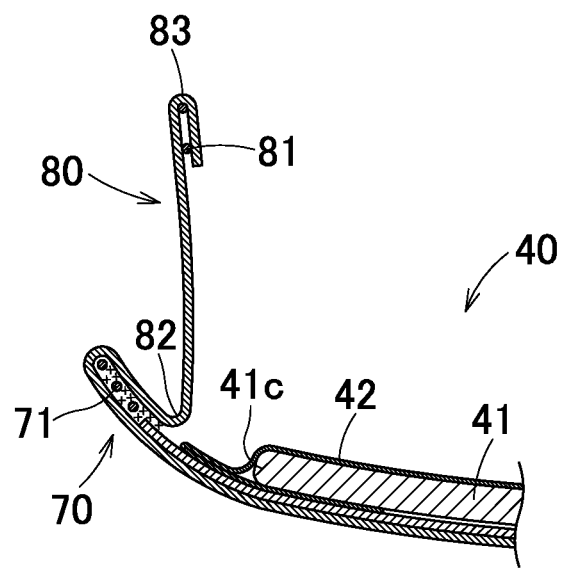
FIG. 5 is a diagram in which the elastic elements of FIG. 4 are contracted.
Figure 6:
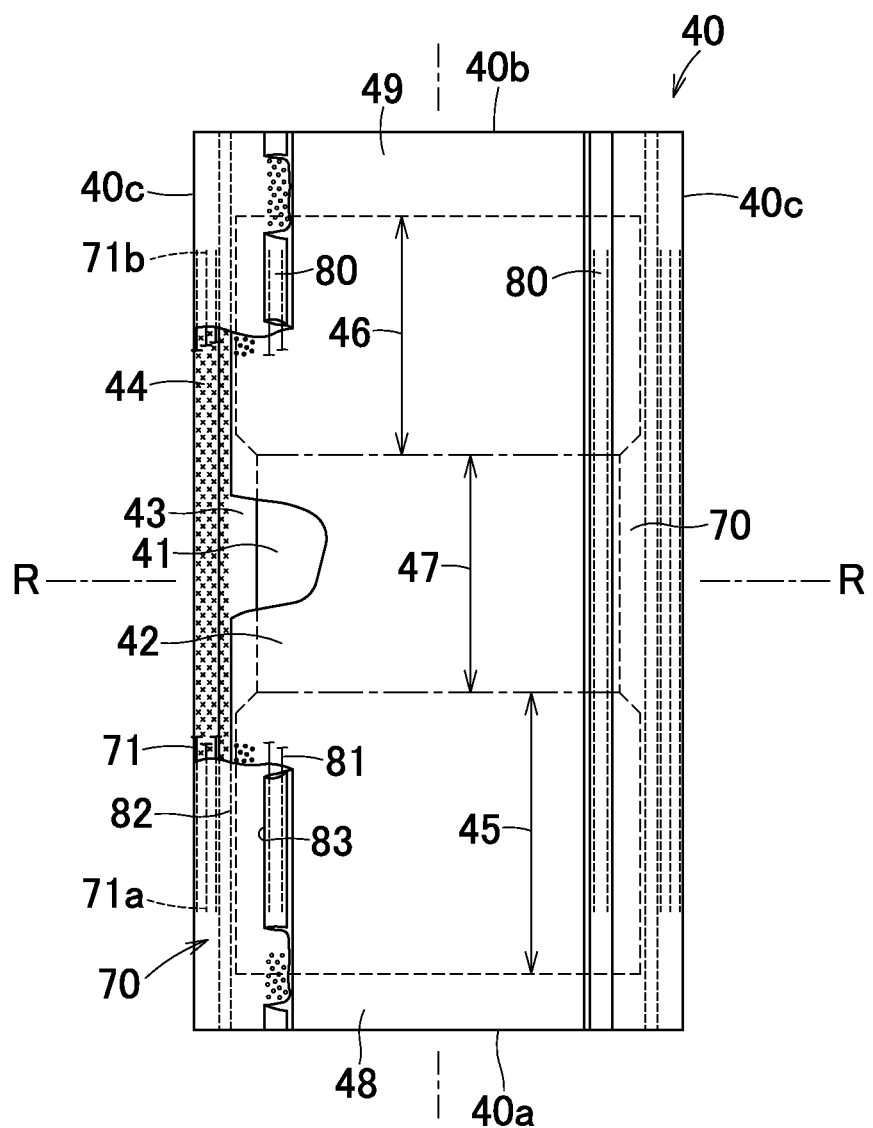
FIG. 6 is a planar view of a liquid absorbent structure.
Figure 7:
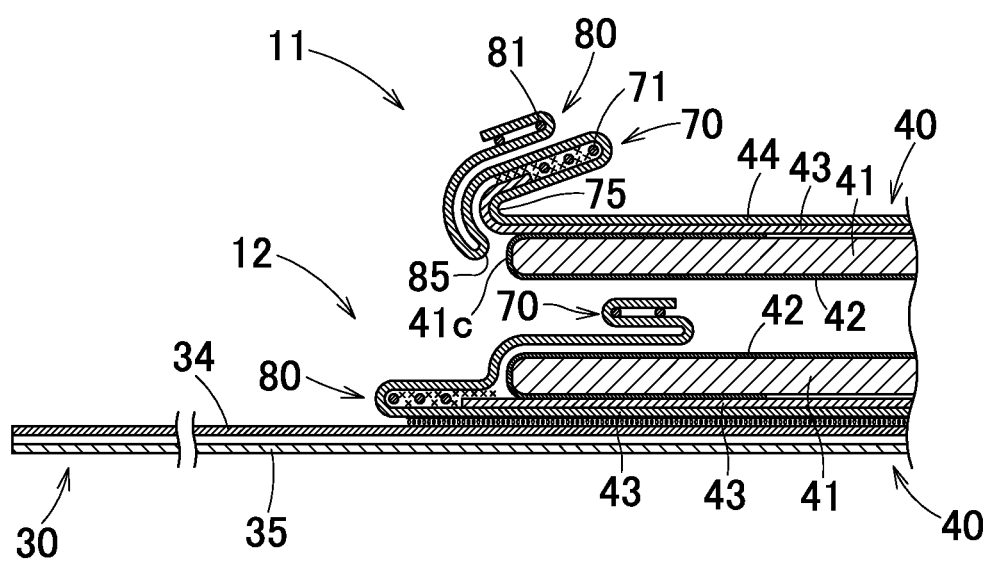
FIG. 7 is a cross section view along VII-VII line of FIG. 1.

FIG. 1 is a planar view in which a waist opening and leg openings of a diaper 10 are kept in a circular state; FIG. 2 is a developed planar view of the diaper 10 viewed from a skin-facing side in which the diaper 10 is kept in a planar state with each elastic element of the diaper being stretched against the contractile force thereof; FIG. 3 is a cross section view along line of FIG. 2; FIG. 4 is a cross section view along IV-IV line of FIG. 2; FIG. 5 is similar to FIG. 4 in which a contractile force of elastic elements are acted; FIG. 6 is a planar view with only a liquid absorbent structure being taken out from FIG. 2; FIG. 7 is a cross section view along VII-VII line of FIG. 1; FIG. 8 is a schematic diagram of a device. In FIGS. 2 and 6, the diaper is partially broken to show an inner structure thereof.

A diaper 10 has a longitudinal direction Y and a lateral direction X and includes a skin-facing side and a garment-facing side opposite thereto, a front waist region 11, a rear waist region 12, and a crotch region 13 extending between the front and rear waist regions 11 and 12. The diaper 10 further has an imaginary longitudinal center line P-P bisecting a dimension in a lateral direction X and an imaginary lateral center line Q-Q bisecting a dimension in a longitudinal direction Y, and is formed substantially symmetrical about the imaginary longitudinal center line P-P.

The diaper 10 includes front and rear panels 20, 30 that are spaced apart from each other in the longitudinal direction Y and a liquid absorbent structure 40 extending between the front and rear panels 20, 30. The front and rear panels 20, 30 have front and rear lateral edges 21, 31 extending in the longitudinal direction Y, front and rear upper end edges 22, 32 extending in the lateral direction X, and front and rear lower end edges 23, 33 to the front and rear upper end edges 22, 32. The front and rear lateral edges 21, 31 are joined to each other to form seams 14, and thereby defining the front and rear upper end edges 22, 32, and defining a pair of leg openings along the front and rear lower end edges 23, 33 of the front and rear panels 20, 30 and lateral edges 40c of the liquid absorbent structure 40.

The rear panel 30 has a dimension larger in the longitudinal direction Y than that of the front panel 20. More specifically, a waist region 30a to be laid about the wearer's waist is overlapped with the front panel 20, with the front and rear panels 20, 30 being joined to each other along the lateral edges thereof (seams 14), and in such a condition, a buttock region 30b extending from the waist region 30a to the crotch region 13 are formed in the rear panel 30. The waist and buttock regions 30a, 30b are defined by an imaginary line 38. A dimension in the longitudinal direction Y of the front panel 20 and the waist region 30a are about 70 to about 240 mm. It is about 106 mm in this embodiment. The dimension in the longitudinal direction Y of the buttock region 30b is about 30 to about 90 mm. It is about 60 mm in this embodiment. The dimension in the lateral direction X of the buttock region 30b is substantially equal to that of the waist region 30a. The waist region 30a and buttock region 30b form a rectangle as a whole.

As will be apparent from the above, a region from the front upper end edge 22 to the front lower end edge 23 of the front panel 20 is defined as the front waist region 11, a region from the rear upper end edge 32 to the imaginary line 38 of the rear panel 30, i.e., the waist region 30a is defined as a rear waist region 12, and a region from the imaginary line 38 to the front lower end edge 23 over the rear lower end edge 33 is defined as the crotch region 13. The front and rear panels 20, 30 and the liquid absorbent structure 40 define the chassis of the present invention.

The front and rear panels 20, 30 includes front and rear inner sheets 24, 34 to be laid on the skin-facing side and front and rear outer sheets 25, 35 to be laid on the garment-facing side. Waist elastic elements are attached between the inner and outer sheets to elasticize the front and rear panels 20, 30 in the lateral direction X. More specifically, the front and rear waist elastic elements 26, 36 composed of a plurality of elastic threads are contractibly attached to the front panel 20 and to the waist region 30a in a stretched state in the lateral direction X. The front and rear waist elastic elements 26, 36 are spaced apart from one another in the longitudinal direction Y, and the pitch thereof is about 3 to about 15 mm. It is about 5 mm in this embodiment. The front and rear waist elastic elements 26, 36 have respective tensile stresses higher in the vicinities of the front and rear upper end edges 22, 32 than these of other regions so that the waist opening comes into close contact with the wearer's body, thereby preventing body exudates such as urine or the like from being leaked. Three to twelve elastic threads of about 470 to about 1240 dtex are used as the front and rear waist elastic elements 26, 36. In the vicinities of the front and rear upper end edges 22, 32, five elastic threads of about 470 dtex are attached at an extension ratio of about 2.7, while in a region closer to the crotch region 13, six elastic threads of about 470 dtex and nine elastic threads of about 620 dtex are attached at an extension ratio of about 2.2, respectively. It is possible to set the extension ratio of the elastic threads in a range of about 1.8 to about 3.5 and to change accordingly.

Buttock elastic elements 37 composed of a plurality of elastic threads is contractibly attached to the buttock region 30b in a stretched state in the lateral direction X. The buttock elastic elements 37 are spaced apart from each other in the longitudinal direction Y, and the pitch thereof is about 10 to about 30 mm. It is about 20 mm in this embodiment, which is larger than the pitch of the front and rear waist elastic elements 26, 36. This is because the buttock region 30b does not need to come into close contact with the body under a high tensile stress. Moreover, by reducing the number of the buttock elastic elements 37, it is possible to prevent the stiffness of the buttock region 30b from becoming greater due to the elastic elements. As the buttock elastic elements 37, it is possible to attach elastic threads of about 470 to about 1240 dtex, setting an extension ratio at about 1.5 to about 3.2. According to this embodiment, three elastic threads of about 470 dtex are used as the buttock elastic elements 37 to be attached at an extension ratio of about 2.2.

Each of the elastic elements 26, 36, 37 are secured to the front inner and outer sheets 24, 25 or the rear inner and outer sheets 34, 35 by directly applying a hot melt adhesive or the like on the surface thereof such that the inner and outer sheets are joined to each other with the adhesive. Therefore, it is possible to ensure to prevent the elastic elements from slipping off and also the stiffness of the sheet from increasing with an extra adhesive.

The liquid absorbent structure 40 includes a liquid absorbent core 41, an inner sheet 42 covering the absorbent surface of the core 41 and to be laid on the skin-facing side, a leakage barrier sheet 43 covering the bottom surface of the core 41, and an outer sheet 44 covering the bottom surface of the leakage barrier sheet 43. The inner sheet 42 and the outer sheet 44 form the coating sheet of the core 41. As material of the core 41, fluff wood pulp, superabsorbent polymer particles or a mixture thereof may be used.

As the inner sheet 42, a liquid permeable fibrous nonwoven fabric or the like may be used. As the inner sheet 42, for example, an air through fibrous nonwoven fabric having a mass per unit area of about 10-30 g/m², a point bonded fibrous nonwoven fabric, a spunbonded fibrous nonwoven fabric or the like may be used.

As the leakage barrier sheet 43, a moisture permeable and a liquid impermeable plastic film may be used. At least the entire bottom surface of the liquid absorbent structure 40 is covered with the sheet 43 so that body fluids such as urine or the like do not leak out of the diaper 10.

As the outer sheet 44, a moisture permeable and liquid impermeable fibrous nonwoven fabric or the like may be used. As the outer sheet 44, for example, a spunbonded/meltblown/spunbonded (SMS) fibrous nonwoven fabric having a mass per unit area of about 10 to about 25 g/m², a point bonded fibrous nonwoven fabric, a spunbonded fibrous nonwoven fabric or the like may be used.

Front and rear end margins 40a, 40b of the liquid absorbent structure 40 overlap with the front and rear panels 20, 30, and the front and rear cover sheets 50, 60 are joined on the front and rear end margins 40a, 40b (refer to FIG. 2 and FIG. 3). The front and rear cover sheets 50, 60 extend from one of the lateral edges 21, 31 of the front and rear panels 20, 30 to the other lateral edges 21, 31 in the lateral direction X, thereby covering the entire region of the front and rear end margins 40a, 40b of the liquid absorbent structure 40. As described above, the front and rear end margins 40a, 40b are covered with the front and rear cover sheets 50, 60, thereby preventing the materials forming the core 41 from spilling over, and the front and rear end margins 40a, 40b from coming into contact with the skin of a wearer to cause skin troubles.

The core 41 of the liquid absorbent structure 40 includes a front portion 45, a rear portion 46, and an intermediate portion 47 extending between the front and rear portions 45, 46. The dimension of the intermediate portion 47 in the lateral direction X is shorter than that of the front and rear portions 45, 46 such that the core 41 is narrowed in the intermediate portion 47. The dimension of the front and rear portions 45, 46 in the lateral direction X is about 120 mm, while such dimension of the intermediate portion 47 is about 80 mm. The dimension of the front portion 45 in the longitudinal direction Y is about 117 mm, while such dimension of the rear portion 46 is about 102 mm, and while such dimension of the intermediate portion 47 is about 116 mm. The core 41 has an imaginary lateral center line R-R bisecting the dimension in the longitudinal direction Y.

As illustrated in FIG. 2, the imaginary lateral center line R-R of the core 41 is closer to the front waist region 11 in relation to the imaginary lateral center line Q-Q of the diaper. Therefore, when the front and rear regions of the core 41 are compared with each other with the longitudinal direction Y of the imaginary lateral center line Q-Q as a reference, a narrow intermediate portion 47 of the core 41 is closer to the front waist region 11 side.

The inner sheet 42, leakage barrier sheet 43, and outer sheet 44 of the liquid absorbent structure 40 are dimensioned larger than the core 41 in the longitudinal direction Y. In the front and rear end margins 40a, 40b of the liquid absorbent structure 40, the front and rear end flaps 48, 49 in which the core 41 is not present, are formed of the inner sheet 42, leakage barrier sheet 43, and outer sheet 44. The inner sheet 42, leakage barrier sheet 43, and outer sheet 44 of the front and rear end flaps 48, 49 are directly joined to one another with suitable joining means such as a hot melt adhesive or the like. However, it should be noted that indirect joining may be applied.

Similarly, in the lateral direction X, the inner sheet 42, leakage barrier sheet 43, and outer sheet 44 extend outward from the edge of the core 41. Lateral margins of the sheets are directly joined to one another with joining means such as a hot melt adhesive or the like. However, it should be noted that indirect joining is not excluded. Outboard of the lateral direction X of the liquid absorbent structure 40, gasket cuffs 70 and containment cuffs 80 which respectively extend in the longitudinal direction Y are formed by the outer sheet 44. Each of the gasket cuffs 70 is formed by folding the outer sheet 44 extending from the lateral edges of the core 41 outward in the lateral direction X. Outboard of the front and rear portions 45, 46 of the core 41 in the lateral direction X, the dimension of the gasket cuffs 70 in the lateral direction X is about 35 mm, while it is about 75 mm outboard of the intermediate portion 47 in the lateral direction X.

Between the outer sheets 44 forming the gasket cuffs 70, a plurality of gasket elastic elements 71 extending in the longitudinal direction Y are contractibly attached in a stretched state, thereby elasticizing the gasket cuffs 70 in the longitudinal direction Y. As the gasket elastic elements 71, it is possible to attach elastic threads of about 470 about 1240 dtex at an extension ratio of about 2.3 to about 3.0. In this embodiment, it is possible to use three elastic threads of about 620 dtex as the gasket elastic elements 71 at an extension ratio of 2.8. In the gasket cuffs 70, the outer sheet 44, leakage barrier sheet 43, and gasket elastic elements 71 are joined to one another with joining means such as an adhesive or the like. The one end 71a of the gasket elastic elements 71 is overlapped with part of the front waist elastic elements 26, and the other end 71b thereof is overlapped with part of the buttock elastic elements 37 (refer to FIG. 2).

As illustrated in FIGS. 4, 5, each containment cuff 80 includes a proximal edge 82 and a distal edge 83 extending in the longitudinal direction Y, which are formed by folding the outer sheet 44 extending from the gasket cuffs 70 so as to be located on the liquid absorbent structure 40. By folding as described above, the distal edge 83 is located above the lateral edge 41c of the core 41, while the proximal edge 82 is located outboard of the lateral edges 41c of the core 41. The dimension from the proximal edge 82 to the distal edge 83 in which each of the containment cuffs 80 is unfolded is about 25 to about 60 mm. In this embodiment, it is about 45 mm, which is larger than the dimension in the lateral direction X of the gasket cuffs 70. However, when each of the containment cuffs 80 is folded, it is smaller than the dimension in the lateral direction X of the gasket cuffs 70 (refer to FIG. 6).

A plurality of containment elastic elements 81 extending in the longitudinal direction Y are contractibly attached to the distal edge 83 in a stretched state to elasticize the containment cuffs 80 in the longitudinal direction Y. By elasticizing as described above, the distal edge 83 is spaced away upward from the inner sheet 42 when the diaper 10 is worn as illustrated in FIG. 5, thereby the containment cuffs 80 carrying out its function. As the containment elastic elements 81, it is possible to attach elastic threads of about 470 to about 1240 dtex at an extension ratio of about 2.3 to about 3.0. In this embodiment, it is possible to use two elastic threads of about 620 dtex as the containment elastic elements 81 at an extension ratio of 2.8.

In the constitution as described above, the diaper 10 is folded such that the front and rear waist regions 11, 12 are in contact with each other along the imaginary lateral center line Q-Q, and the front and rear upper end edges 22, 32 are substantially aligned with each other so as to be in the same level (refer to FIG. 1 and FIG. 7). In such a folded state, first folds 75 extending in the longitudinal direction Y are formed on the side closer to the front waist region 11 in relation to the imaginary lateral center line Q-Q of the gasket cuffs 70. The first folds 75 are located along the lateral edges 41c of the core 41 and the gasket cuffs 70 lying outboard of the lateral edges 41c are folded to the garment-facing side of the outer sheet 44 along the first folds 75.

As previously mentioned, since the gasket elastic elements 71 are contractibly attached in the lateral edges of the gasket cuffs 70 in the longitudinal direction Y, and therefore, once the gasket cuffs 70 are folded onto the garment-facing side, they are capable of keeping a folded state under a contractile force of the gasket elastic elements 71, so that the folded state should not be easily unfolded.

Second folds 85 extending in the longitudinal direction Y are defined in the containment cuffs 80. The second folds 85 are located on the side closer to the front waist region 11 in relation to the imaginary lateral center line Q-Q, and folded to the garment-facing side of the outer sheet 44.

In this invention, though it is required that the first and second folds 75, 85 extend in the longitudinal direction Y at least in the crotch region 13, in this embodiment, they are configured to extend in the front waist region 11. Thus, the lateral edges of the gasket cuffs 70 and the distal edge 83 of the containment cuffs 80 are folded to the garment-facing side of the outer sheet 44 along the lateral edges 41c of the core 41 even in the front waist region 11.

In the front waist region 11, an area in which the front panel 20 is overlapped with the liquid absorbent structure 40 is larger than in the rear waist region 12 (refer to FIG. 2). Additionally, the front waist elastic elements 26 is attached to the front panel 20, overlapping at least with the lateral edges 41c of the core 41. Thus, in the lateral edges 41c of the core 41, the front panel 20 is pushed inwardly in the lateral direction X. In such a manner, in the lateral edges 41c of the core 41, the first folds 75 are continuously formed from the crotch region 13 also into the front waist region 11. Moreover, by a contractile force of the front waist elastic elements 26, it keeps a form of the first folds 75 and keeps the folded state since the gasket elastic elements 71 are pushed inwards in the lateral direction X.

As described above, since the gasket cuffs 70 and the containment cuffs 80 are folded to the garment-facing side in the crotch region 13, it keeps preventing the gasket cuffs 70 and containment cuffs 80 from apparently making the leg openings small. If the areas of the leg openings are apparently made small by these cuffs, it is difficult for the wearer to recognize the leg openings when putting on the diaper 10. According to the embodiment of the present invention, however, the leg openings, i.e., the positions thereof to pass through the wearer's legs are readily recognized. In particular, since the respective containment cuffs 80 have a large dimension in the lateral direction X, when they are expanded from a folded state, they may considerably extend to the leg openings; however, the containment cuffs 80 may be folded along the second folds 85 to be kept on the garment-facing side.

Moreover, since the first and second folds 75, 85 are formed in the side closer to front waist region 11 of the crotch region 13, it is readily recognized that the side in which the gasket cuffs 70 and the containment cuffs 80 are folded is the side closer to the front waist region 11 which is to be the abdominal side when putting on.

When the above diaper 10 is worn, not only the front and rear waist elastic elements 26, 36 are stretched but also the gasket elastic elements 71 and the containment elastic elements 81 are stretched, thereby the first and second folds 75, 85 substantially disappear. More specifically, the front and rear waist elastic elements 26, 36 are stretched, the first and second folds 75, 85 lying in the front and rear waist regions 11, 12 are unfolded in the lateral direction X and substantially disappear accordingly, thereby the entirety of the front and rear waist regions 11, 12 come into close contact with the wearer's body. Moreover, the gasket cuffs 70 and the containment cuffs 80 are also pulled outward in the lateral direction X under the stretch of the front and rear waist elastic elements 26, 36, thereby the first and second folds 75, 85 are also unfolded. Furthermore, while the gasket cuffs 70 and the containment cuffs 80 are pulled outward in the lateral direction X, the gasket elastic elements 71 and the containment elastic elements 81 are contracted, hence the gasket cuffs 70 and the containment cuffs 80 come into close contact with the wearer's thighs and/or inguinal region, thereby preventing urine or the like from leaking from the leg openings (refer to FIG. 5).

The first and second folds 75, 85 may be formed as illustrated in FIG. 8, for example. FIG. 8 is a diagram illustrating how to form folds by applying a device 90 to the diaper 10 in which seams 14 are defined and which are folded along the imaginary lateral center line Q-Q. In the device 90, the diaper 10 folded as described above is conveyed to a suction belt 91 in an upstanding state, with the crotch region 13 at the top of the drawing and the front and rear waist regions 11, 12 at the bottom of the drawing. The suction belt 9 is provided with a plurality of apertures 92. The diapers 10 are suctioned inward by a suction mechanism 93, thereby fixing the diaper 10 on the surface of the suction belt 91 so as to keep them in the upstanding state to be conveyed in an arrow direction A.

In a direction perpendicular to the arrow direction A, a conveying path 95 is defined between a pair of feeding belts 94. The conveying path 95 conveys the diaper 10 by the feeding belts 94 from the suction belt 91 to the arrow direction B. A spaced-apart distance L between the feeding belts 94 is about 125 mm, which is to be smaller than the dimension in the lateral direction X of the diaper 10.

The suction belt 91 is provided with a pusher 96 movable along the arrow direction B pushing the diaper 10 toward the conveying path 95. The pusher 96 includes a first pusher 97 lying at the top of the drawing and pushing the crotch region 13 of the diaper 10 and a second pusher 98 located in the bottom part of the drawing and pushing the front and rear waist regions 11, 12 of the diaper 10. The first and second pushers 97, 98 are spaced apart in up and down directions. The first pusher 97 pushes the crotch region 13 of the diaper 10 toward the conveying path 95 side across the upper end 91a of the suction belt 91, while the second pusher 98 pushes the front and rear waist regions 11, 12 of the diaper 10 toward the conveying path 95 across the lower end 91b of the suction belt 91.

The first and second pushers 97, 98 have a dimension M along the arrow direction A of about 108 mm and are movable between the feeding belts 94. The dimension M of the first and second pushers 97, 98 is smaller than the dimension in the lateral direction X of the front and rear portions 46, 47 of the core 41 of the diaper 10. Moreover, a spaced-apart distance between the first and second pushers 97, 98 in up and down directions is about 100 mm, these pushers 97, 98 being movable in the arrow direction B without contacting the suction belt 91.

The diaper 10 is conveyed with the front waist region 11 facing the pusher 96 side. When the diaper 10 is pushed by the pusher 96, the core 41 is strongly pushed to the arrow direction B such that it becomes separated from the suction belt 91, and the lateral edges of the diaper 10 with which the pusher 96 is not directly in contact is folded along the lateral edges of the pusher 96 while being pushed by the pusher 96. Since the spaced-apart dimension L of the feeding belts 94 is smaller than the dimension in the lateral direction of the diaper 10, the lateral edges of the diaper 10 about the lateral edges of the pusher 96 so as to be easily folded to overlap with the front outer sheets 25 of the front waist region 11.

In the lateral margins of the diaper 10, the core 41 is not present. In the lateral margins, the gasket cuffs 70 and the containment cuffs 80 are easily bendable along the lateral edges of the core 41 due to the difference of stiffness between the lateral margins and the cuffs 70, 80. Thus, the first folds 75 are formed on the gasket cuffs 70, while the second folds 85 are formed on the containment cuffs 80.

The first and second folds 75, 85 are formed not only in an area in which the pusher 96 comes into contact but also in extensions thereof. This is because the front inner and outer sheets 24, 25 of the front panel 20 are bent in the lateral edges 41c of the core 41 that is pushed by the pusher 96.

A predetermined number of diapers 10 are put side by side in the conveying path 95, and the put diapers 10 are pushed by the pusher 96. That is to say, since the diaper 10 is pushed while being bent at the first and second folds 75, 85, a folding propensity is formed along the first and second folds 75, 85, thereby easily keeping the bending state.

A method for forming the first and second folds 75, 85 is not limited to the one used by the above device, and it is possible to adopt other different methods. Moreover, so-called three-piece structured diapers, in which the front and rear panels 20, 30 and the liquid absorbent structure 40 are formed separately of one another and the former two are coupled by the last one, is used as an example to describe the diaper, but it is not limited to this. It is acceptable that the diaper has a constitution such that the front and rear waist regions 11, 12 and the crotch region 13 are continuous.

The front and rear waist elastic elements 26, 36 are constituted to continuously extend from one lateral edges 21, 31 to the other lateral edges 21, 31; however, these elastic elements 26, 36 in an area overlapping with the core 41, for example, cut away so as not to exert the contractile force thereof. It is acceptable to use other means such as securing with bonding means or the like such that the elastic elements do not exert the contractile force on the core 41. In this regard, in order to form the folds, it is preferred that the front waist elastic elements 26 overlap with at least the lateral edges 41c of the core 41.

In the specification and claims of the present invention, the terms "first" and "second" are used so as to merely distinguish the elements, positions or the like having similar names. Furthermore, in the specification and claims of the present invention, the term "first waist region" means one of the front and rear waist regions, and the term "second waist region" means the other.

REFERENCE SIGNS LIST 10 diaper (wearing article)
11 front waist region (first or second waist region)
12 rear waist region (first or second waist region)
13 crotch region
20 front panel
21 lateral edges
22 first end edge
26 front waist elastic elements
30 rear panel
31 lateral edges
32 second end edge
36 rear waist elastic elements
40 liquid absorbent structure
41 core
41c lateral edges
42 inner sheet (coating sheet)
44 outer sheet (coating sheet)
70 gasket cuffs
71 gasket elastic elements
71a one end
71b other end
75 first folds
80 containment cuffs
81 containment elastic elements
82 proximal edge
83 distal edge
85 second folds
X lateral direction
Y longitudinal direction
Q-Q imaginary lateral center line

The invention claimed is:

1. A wearing article having a longitudinal direction and a lateral direction, comprising:
 a chassis including
 a skin-facing side facing the wearer's skin and a garment-facing side opposed to the skin-facing side;
 a first waist region that is one of front and rear waist regions;
 a second waist region that is a remainder of the front and rear waist regions; and
 a crotch region extending between the first and second waist regions; and
 a pair of gasket cuffs is formed outboard of the liquid absorbent structure in the lateral direction, and gasket elastic elements are contractibly attached to the gasket cuffs in the longitudinal direction, wherein
 the chassis further includes first and second upper end edges extending in the lateral direction in the first and second waist regions and lateral edges extending
 in the longitudinal direction;
 the lateral edges of the first and second waist regions are joined to one another such that a waist opening is defined by the front and rear upper end edges and such that a pair of leg openings are defined by the lateral edges of the crotch region;
 each of the gasket cuffs lateral edges in at least the crotch region are folded laterally onto the garment-facing side of the chassis along first folds extending in the longitudinal direction; and
 the first folds are at least in the crotch region and at a side closer to the first waist region in relation to an imaginary lateral center line that bisects a dimension in the longitudinal direction from the first upper end edge to the second upper end edge,
 wherein the folded gasket elastic elements of the gasket cuffs that are folded laterally in at least the crotch region resist unfolding of the wearing article from a folded state,
 and wherein the article further comprises containment cuffs; the containment cuffs and gasket cuffs are folded oppositely to each other in the waist regions.

2. The wearing article according to claim 1, further comprising a liquid absorbent structure extending from the crotch region into the first and second waist regions on the skin-facing side of the chassis, wherein
 the liquid absorbent structure includes a liquid absorbent core and a coating sheet to cover the core, and
 the first folds are defined along the lateral edges of the core.

3. The wearing article according to claim 1, wherein waist elastic elements are contractibly attached to the first waist region in a stretched state in the lateral direction, and the waist elastic elements are overlapped with at least the lateral edges of the core.

4. The wearing article according to claim 3, wherein the waist elastic elements and the gasket elastic elements are intersected with each other in the first waist region.

5. The wearing article according to claim 1, wherein
the liquid absorbent structure includes an upper surface facing the wearer's body and a bottom surface opposite thereto;
elasticized containment cuffs are contractibly attached to the upper surface in a stretched state in the longitudinal direction;
each of the containment cuffs includes a proximal edge continuous to the upper surface and a distal edge which is capable of being spaced apart from the upper surface; and
the distal edge is folded onto the garment-facing side of the chassis along second folds extending in the longitudinal direction.

6. The wearing article according to claim 2, wherein waist elastic elements are contractibly attached to the first waist region in a stretched state in the lateral direction, and the waist elastic elements are overlapped with at least the lateral edges of the core.

7. The wearing article according to claim 1, wherein the waist elastic elements and the gasket elastic elements are intersected with each other in the first waist region.

8. The wearing article according to claim 6, wherein the waist elastic elements and the gasket elastic elements are intersected with each other in the first waist region.

9. The wearing article according to claim 2, wherein
the liquid absorbent structure includes an upper surface facing the wearer's body and a bottom surface opposite thereto;
elasticized containment cuffs are contractibly attached to the upper surface in a stretched state in the longitudinal direction;
each of the containment cuffs includes a proximal edge continuous to the upper surface and a distal edge which is capable of being spaced apart from the upper surface; and
the distal edge is folded onto the garment-facing side of the chassis along second folds extending in the longitudinal direction.

10. The wearing article according to claim 3, wherein
the liquid absorbent structure includes an upper surface facing the wearer's body and a bottom surface opposite thereto;
elasticized containment cuffs are contractibly attached to the upper surface in a stretched state in the longitudinal direction;
each of the containment cuffs includes a proximal edge continuous to the upper surface and a distal edge which is capable of being spaced apart from the upper surface; and
the distal edge is folded onto the garment-facing side of the chassis along second folds extending in the longitudinal direction.

11. The wearing article according to claim 4, wherein
the liquid absorbent structure includes an upper surface facing the wearer's body and a bottom surface opposite thereto;
elasticized containment cuffs are contractibly attached to the upper surface in a stretched state in the longitudinal direction;
each of the containment cuffs includes a proximal edge continuous to the upper surface and a distal edge which is capable of being spaced apart from the upper surface; and
the distal edge is folded onto the garment-facing side of the chassis along second folds extending in the longitudinal direction.

12. The wearing article according to claim 6, wherein
the liquid absorbent structure includes an upper surface facing the wearer's body and a bottom surface opposite thereto;
elasticized containment cuffs are contractibly attached to the upper surface in a stretched state in the longitudinal direction;
each of the containment cuffs includes a proximal edge continuous to the upper surface and a distal edge which is capable of being spaced apart from the upper surface; and
the distal edge is folded onto the garment-facing side of the chassis along second folds extending in the longitudinal direction.

* * * * *